United States Patent [19]
Förster

[11] Patent Number: 4,668,187
[45] Date of Patent: May 26, 1987

[54] DISPENSER FOR A CONTROLLED DISCHARGE OF POLYMERIZABLE COMPOSITIONS CONSISTING OF A POWDER AND A LIQUID IN THE MAKING OF DENTAL PLATES

[75] Inventor: Rolf Förster, Pforzheim, Fed. Rep. of Germany

[73] Assignee: Bernhard Forster GmbH, Pforzheim, Fed. Rep. of Germany

[21] Appl. No.: 765,324

[22] Filed: Aug. 13, 1985

[30] Foreign Application Priority Data
Oct. 2, 1984 [DE] Fed. Rep. of Germany ....... 3436056

[51] Int. Cl.⁴ .............................................. A61C 13/00
[52] U.S. Cl. ...................................... 433/25; 222/179
[58] Field of Search ............... 222/179, 401, 402, 135; 433/25, 80, 77

[56] References Cited
U.S. PATENT DOCUMENTS
2,628,744  2/1953  Mowbray ............................ 222/179
4,266,693  5/1981  Pzeiffer ............................... 222/135
4,274,556  6/1981  Thiessen ............................. 222/135

Primary Examiner—Robert Peshock
Attorney, Agent, or Firm—Balogh, Kramer, Dvorak, Genova & Traub

[57] ABSTRACT

A dispenser is disclosed for a controlled discharge of polymerizable compositions consisting of a powder and a liquid in the making of dental plates for prosthodontic and orthodontic purposes in a process in which the liquid is applied to a layer of the powder on a model and the powder and liquid are polymerized on said model. The discharge of the powder and liquid from respective containers is controlled by foot-operable bellows and hand-held nozzles for discharging the powder and liquid, respectively are supplied with the liquid and powder from the containers via hoses.

18 Claims, 5 Drawing Figures

DISPENSER FOR A CONTROLLED DISCHARGE OF POLYMERIZABLE COMPOSITIONS CONSISTING OF A POWDER AND A LIQUID IN THE MAKING OF DENTAL PLATES

BACKGROUND OF THE INVENTION

1. Field of the Invention

This invention relates to a dispenser for a controlled discharge of polymerizable compositions consisting of a powder and a liquid in the making of dental plates for prosthodontic and orthodontic purposes in a process in which the liquid is applied to a layer of the powder on a model and the powder and liquid are polymerized on said model.

2. Description of the Prior Art

It is known that plates for prosthodontic or orthodontic purposes can be made in that spray nozzles connected to bottles containing polymerizable compositions consisting of a powder and a liquid are held over the model and manual pressure is applied to each bottle so that powder is sprinkled and liquid is sprayed out of the nozzle that is held over the model. It is also known to use a pump for applying the liquid to the model on which a powder layer has been formed.

In other known dispensers the powder and the liquid are applied by means of a hand-held gun having two outlets. In such a dispenser the powder and liquid to be applied to the model are respectively fed by means of a feed screw and a pump. In said dispensers the nozzles for discharging the powder and the liquid must be sufficiently spaced apart because the liquid must not contact the powder in the jet when the liquid and powder are discharged at the same time. During a polymerization, the powder will absorb the liquid and will thus be wetted by the liquid over a distance of 6 to 10 millimeters, depending on the rate at which liquid is discharged. In such a hand-held gun, a simultaneous discharge of powder and liquid may result in a polymerization in the powder in the nozzle so that the latter will be clogged. Owing to the large spacing required between the nozzles, the powder and liquid can be simultaneously applied to the model only on a relatively small area so that the tooth fissures of the plaster model cannot be exactly filled. Besides, the feeding means of said known dispensers do not permit of a fine adjustment of the discharge rates.

In the manufacture of plates for prosthodontic or orthodontic purposes the powder is sprinkled onto the plaster model to form a strip-shaped layer and the liquid is then applied to said layer. In dependence on the velocity at which the liquid impinges on the powder, the latter will be formed with craterlike or furrowlike elevations and depressions so that the surface of the plate that is formed must subsequently be smoothened by milling polishing at high costs in order to minimize the annoyance of the patient by the plate. It must be borne in mind that the tongue is the most sensitive part in the mouth.

Noxious vapors are evolved during the polymerization and as the liquid impinges on the powder. For this reason the operation can be carried out only by a person wearing a gas mask or if the vapors are sucked off by an exhaust fan. In the known methods in which the spraying bottle, the pumping apparatus or the gun are held by one hand and the model is held by the other hand, the suction pipe must be widely spaced apart from the plaster model and from the spraying apparatus because the orientation of the model must be varied during the operation. Besides, an adequate vacuum cannot be applied because otherwise the powder may be sucked away from the model or the powder or liquid may be sucked out of the jet into the suction device. It must be borne in mind that without an adequate exhausting of the monomer vapors the latter will be dispersed throughout the laboratory, which in most cases is included in the dentist's office, so that there will also be an annoyance of the people working in the office and of the patients.

SUMMARY OF THE INVENTION

It is an object of the invention to provide a dispenser which permits a very fine adjustment of the discharge rate so that very thin dental plates can be made, which can be conveniently worn by the patients and will minimize the irritation of the tongue.

Another object of the invention is to avoid during the making of such plates a formation of craterlike elevations and depressions, which must subsequently be eliminated by additional work at additional costs.

A further object is to ensure that noxious vapors will be sucked off in a satisfactory manner.

A further object resides in that the dispenser should be structurally simple so that it will constitute a highly economical appliance. It must be borne in mind that only one dental technician is employed in most cases by a given dentist and must perform work of all kinds for making prosthodontic and orthodontic appliances as well as crowns for individual teeth. Such technician will be engaged in the making of the dental plates only for a few hours a week so that a highly expensive dispenser used for that purpose would not be economical because it is used only for a relatively short time.

In a dispenser for a controlled discharge of polymerizable compositions consisting of a powder and a liquid in the making of dental plates for prosthodontic and orthodontic purposes in a process in which the liquid is applied to a layer of the powder on a model and the powder and liquid are polymerized on said model the above-mentioned and other objects are accomplished in accordance with one aspect of the invention by the provision of a container for the powder, a container for the liquid, a carrying structure holding said containers in position, two foot-operable bellows connected to respective ones of said containers by hoses, two manually movable discharge nozzles, two discharge lines, which are flexible at least in part of their length and each of which connects one of said nozzles to a bottom outlet of one of said containers, and two foot-operable bellows communicating with the upper portion of respective ones of said containers and operable to force powder and liquid out of the respective containers through said discharge lines and nozzles.

In another aspect of the invention the dispenser comprises a container for the powder, a container for the liquid, a carrying structure holding said containers in position, two manually movable discharge nozzles, two discharge lines, which are flexible at least in part of their length and one of which connects one of said nozzles to a bottom outlet of said container for the powder, whereas the other discharge line connects the other of said nozzles to a valve, which comprises a spring tending to close said valve and which is connected to a bottom outlet of the container for liquid, and two foot-operable bellows, one of which is operable to force powder out of said container for powder through the associated discharge line and nozzle, whereas the other bellows is operable to open said valve against the force of said spring in order to permit said liquid to flow by gravity out of said container for liquid through said valve, the associated discharge line and the associated nozzle.

In both aspects of the invention, the two nozzles may be mechanically connected to each other.

In the use of such dispensers, the rates at which the powder and the liquid are discharged are controlled by the foot-operated bellows rather than by hand so that the operator can freely use his hands to move the nozzle or nozzles and the model.

The provision of pedals for the operation of the bellows will permit a precise control of the discharge rates so that the liquid can be discharged in drops dispensed after selected intervals of time or in the form of a very thin jet and the powder can be discharged as a stream of trickling powder but also as a full jet. In a preferred arrangement the model is fixed to a platform and the operator holds the nozzles by respective hands so that the layer of plastic powder is applied first and the liquid is subsequently applied to the powder in the form of drops or as a very thin jet and under a pressure which is so low that a formation of craters in the powder layer will reliably be avoided. The tooth fissures formed in the model can be entirely filled with the powder because the movement of the hose leading to the nozzle for discharging the powder can be very closely controlled.

Because the model is fixed to the platform, which must be pivotally moved by hand only to a small extent in accordance with the curvature of the side portions of the palate during the making of a palate plate, for instance, so that the strip-shaped powder layer will not slip off, the position of the model relative to the suction pipe need not be changed. For this reason a vacuum may be applied which is sufficient for exhausting the toxic gases but which will not disturb the powder layer.

In a further aspect of the invention the carrying structure comprises a suction hood for exhausting the monomer vapors formed during the use of the dispenser. For this purpose a suction hose is connected to the suction hood. The vapors which have been sucked off are passed through an activated carbon filter.

In the manufacture of activators, which are integral appliances for an orthodontic treatment of the upper and lower jaws, both plaster models are fitted into a fixator and adjusted for a desired design occlusion. The plaster model is then sealed from the outside and a rubber ring is simply fitted on the two hoses. The nozzle for discharging liquid is stretched and fixed in a position in which it protrudes 1 to 2 millimeters beyond the nozzle for discharging the powder. The two bellows can then be foot-operated to inject the monomeric liquid and the prepolymerized powder into the activator from behind. That operation may be further simplified in that the pedals for operating the bellows are provided with means for releasably locking each pedal in a preadjusted position so that the proportions in which the powder and liquid are discharged can be exactly controlled.

The success of the orthodontic treatment of children depends highly on whether they can be motivated to wear the orthodontic appliances. It is known that colored plates are particularly well received by children. In the use of the dispenser in accordance with the invention, a liquid color concentrate may be placed into a container, which is smaller than the container for the monomeric liquid and is mounted on the carrying structure and the liquid color concentrate may be used to give the desired color to the monomeric liquid. A plurality of said additional containers containing liquid color concentrates differing in color may be mounted on the carrying structure. Any container containing a liquid color concentrate may be connected to a bellows by a hose and said bellows and hose may be colored in dependence on the liquid color concentrate in the container. In that case, the liquid color concentrate can be added to the powder and liquid on the model before the product is cured so that the product can be provided with colored sectors or with a cloudlike appearance (like marble) or with color patterns in an unlimited number.

DETAILED DESCRIPTION OF THE PREFERRED EMBODIMENTS

Figure 1:
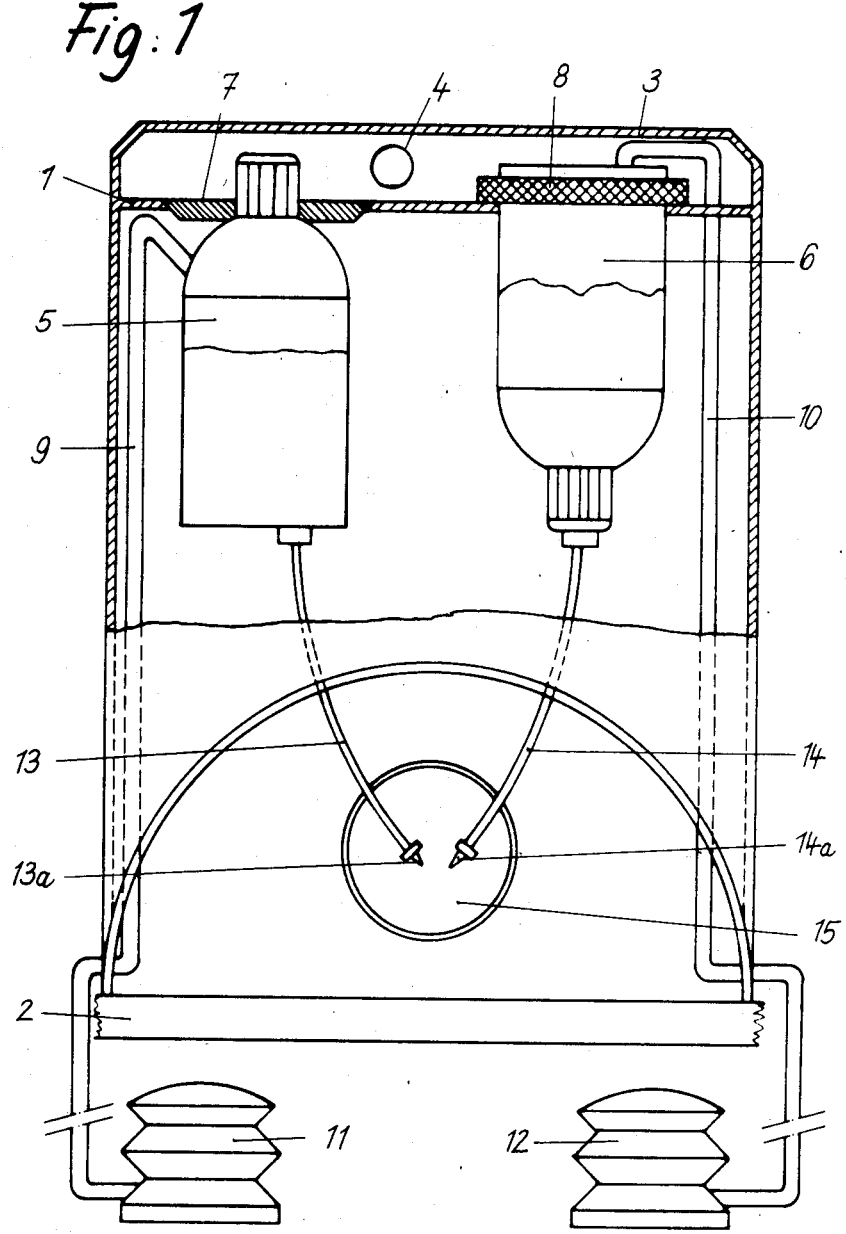
FIG. 1 is a diagrammatic elevation showing a first embodiment of a dispenser for polymerizable compositions consisting of a powder and a monomeric liquid.

Preferred embodiments of dispensers in accordance with the invention will now be described more in detail with reference to the drawing, from which further details are apparent.

In the first embodiment shown in FIG. 1 a carrying structure 1 is placed on a table top 2 and provided with a suction hood 3 having a suction port 4 for exhausting the monomer vapors evolved during the operation of the dispenser. A bottle 5 containing a prepolymerized powder and a bottle 6 containing a monomeric liquid are suspended from the carrying structure and are secured to it by a plug joint 7 and a mounting ring 8, respectively. Each bottle is formed at its top with an inlet port, which is connected by a tube 9 or 10 to a foot-operable bellows 11 or 12. Each of the bottles 5 and 6 is provided at its bottom with an outlet port, which is connected to a discharge nozzle 13a or 14a by a discharge line 13 or 14, which is flexible at least in part of its length. The nozzle 13a and 14a can be moved by hand to positions adjacent to a platform 15 at the forming station and are adapted to discharge the powder and liquid, respectively, at a rate which is controlled by the associated foot-operated bellows.

The powder from bottle 5 may be applied to the model to form a base layer and the monomeric liquid from the bottle 6 may be applied to the powder on the model to effect a polymerization. Both compositions can be applied at a low rate, which is controlled by the associated foot-operated bellows.

Figure 2:
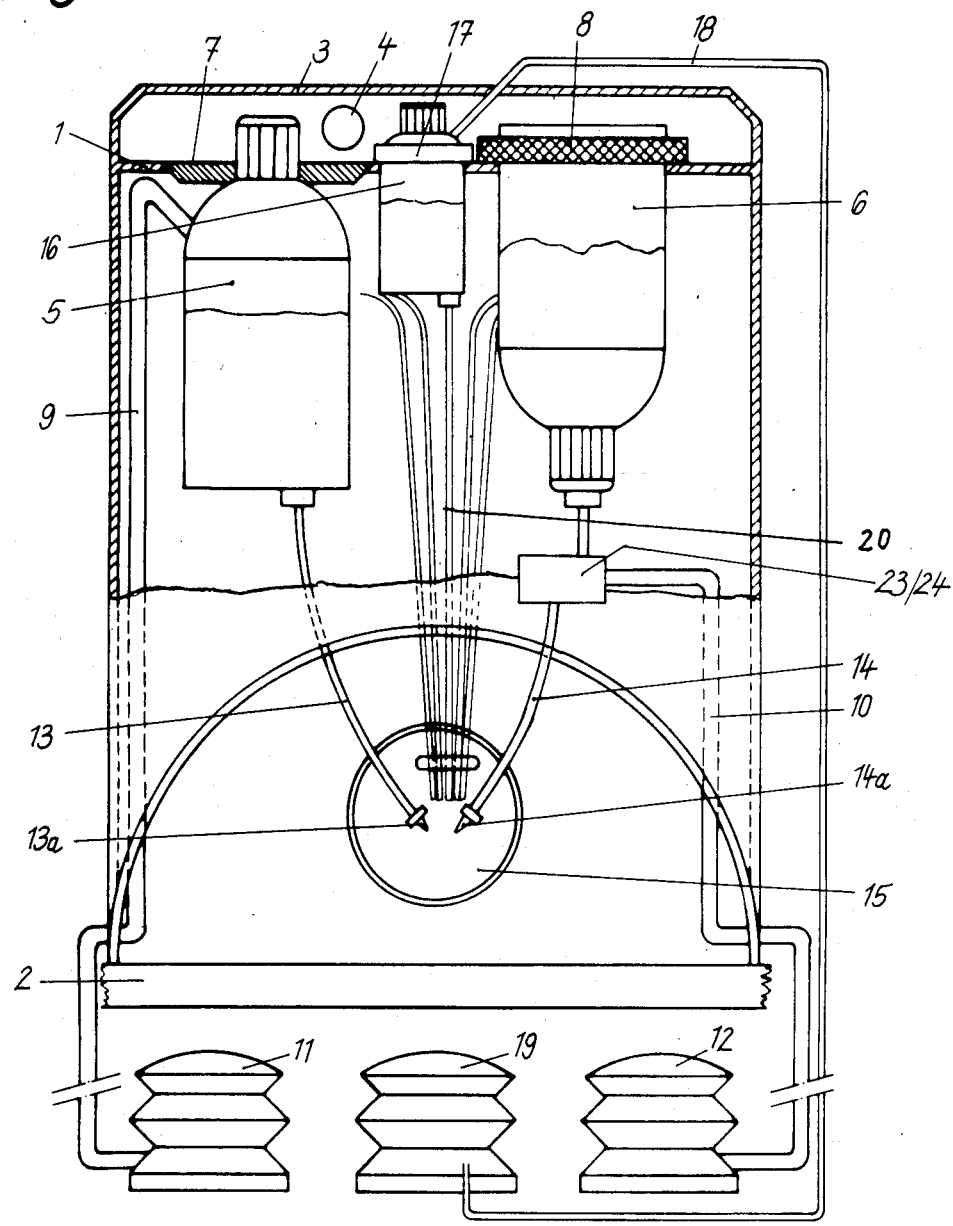
FIGS. 2 and 3 are, respectively, an elevation and top plan view showing that dispenser with means for dispensing also liquid color concentrates.
Figure 3:
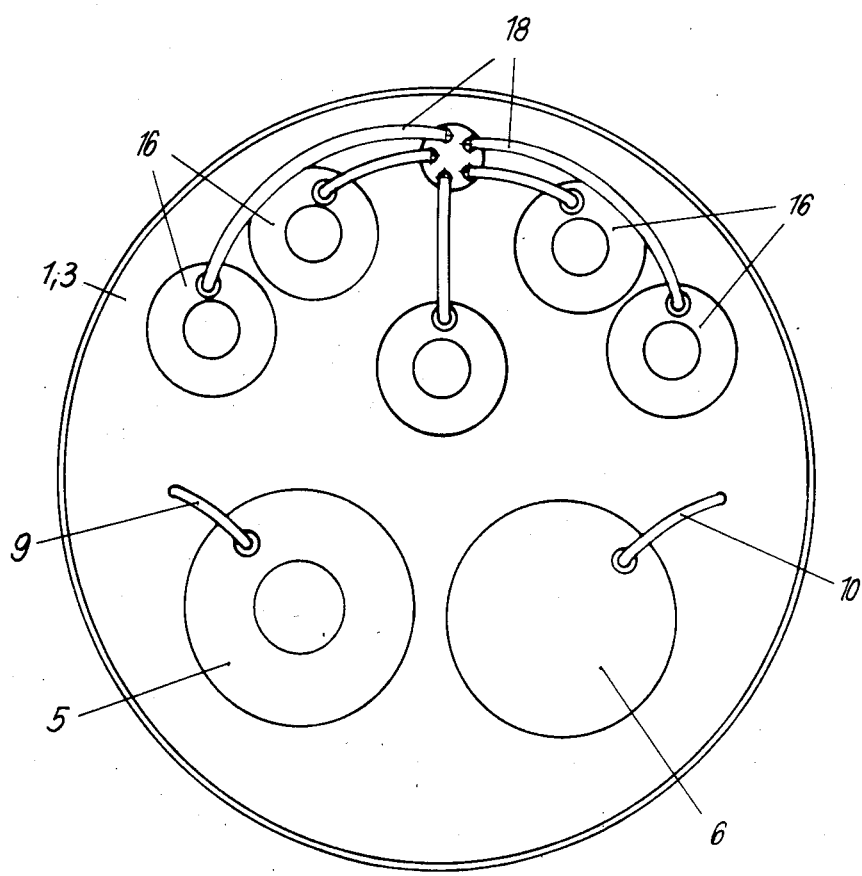

In accordance with FIGS. 2 and 3 a plurality of bottles 16 containing liquid color concentrates differing in color are suspended in the carrying structure 1 and mounted by means of retaining rings 17. Each of the bottles 18 is provided at its top with an inlet port, which may be detachably connected by a hose 18 to a foot-operable bellows 19. Each of the bottles 16 is provided at its bottom with an outlet port, which is connected to a discharge line 20, which has a free end disposed adjacent to the platform 15. Before the monomeric liquid and the powder layer on the model have polymerized, liquid color concentrate from the bottles can be added to the monomeric liquid from the bottle 6 to impart desired colors to the plates. Just as in the embodiment shown in FIG. 4, the port at the bottom of the bottle 6 is connected to a normally closed, spring-loaded valve 23/24, which is connected by the discharge line 14 that is flexible at least in part of its length to the discharge nozzle 14a, and the foot-operable bellows 12 is connected by a hose 10 to the valve 23/24 and is operable to open the valve against the force of its spring. When the valve 23, 24 is open, liquid will flow by gravity from the bottle 6 through the line 14 to and out of the discharge nozzle 14a.

Figure 4:
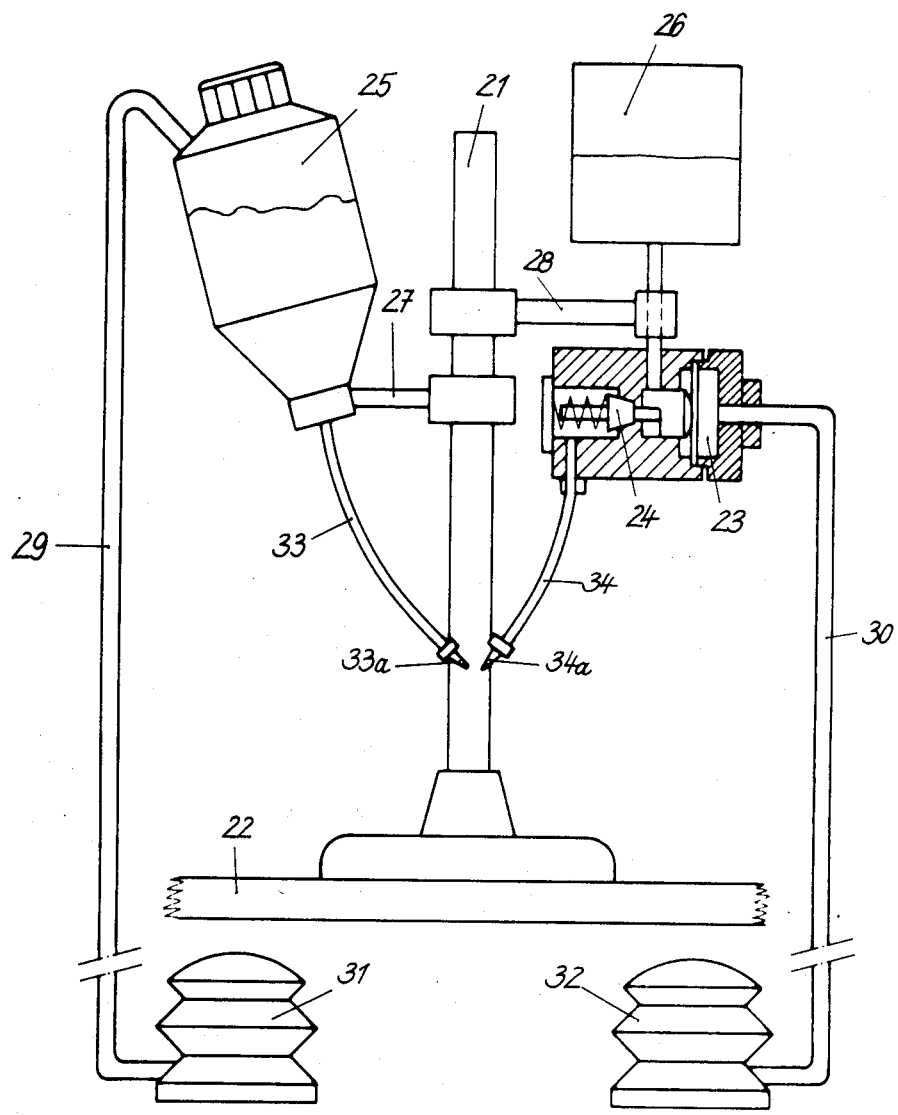
FIG. 4 is a diagrammatic elevation showing a dispenser comprising a valve for controlling the discharge of liquid.

The embodiment shown in FIG. 4 comprises a carrying structure 21, which is placed on a table top 22. The means for exhausting the monomeric vapors are not shown in FIG. 4. The carrying structure 21 comprises a post and carrying arms 27 and 28, which are carried by the post and carry the bottle 25 containing a prepolymerized powder and a container 26 for containing a monomeric liquid. The powder-containing bottle 25 is provided at its top with a port that is connected by a hose 29 to the foot-operable bellows 31 and is provided at its bottom with a port that is connected by a discharge line 33, that is flexible at least in part of its length, to a discharge nozzle 33a, which can be moved by hand to the forming station. The container 26 for liquid is provided at its bottom with a port that is connected to a normally closed valve, which comprises a valve cone 24 and a diaphragm 23, which is pneumatically operable to move the valve cone 24 in an opening sense against spring force. A foot-operable bellows 32 is connected by a hose 30 to the valve 23, 24 and is operable to supply compressed air to the diaphragm 24 so that the latter will open the valve. When the valve 23, 24 is open, liquid from the container 26 can flow by gravity through the valve 23, 24 and the discharge line 34 to the discharge nozzle 34a and out of the latter. The bellows 23, 24 are operable to effect a discharge of powder and liquid from the nozzles 33a and 34a, respectively, at the low rates which are desired.

Figure 5:
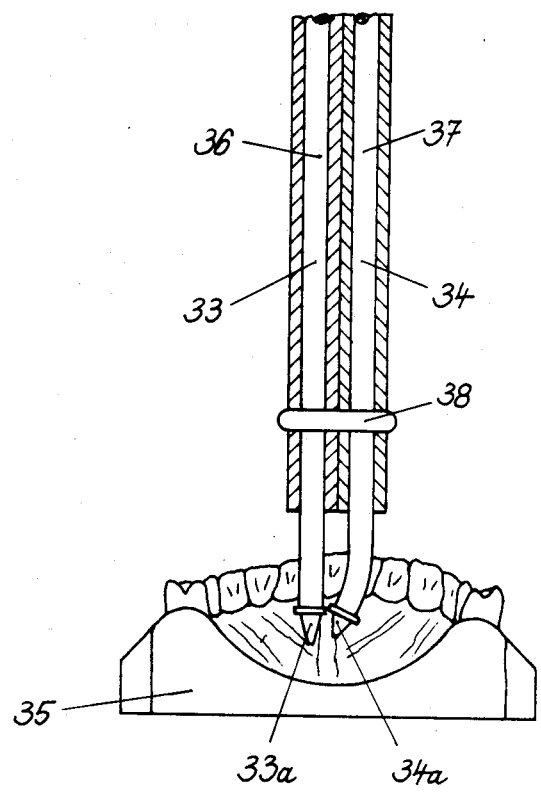
FIG. 5 shows discharge nozzles which are mechanically connected.

FIG. 5 shows a model 35 which consists of plaster of Paris and is disposed at the forming station. The nozzles 33a and 34a at the ends of the respective hoses 33 and 34 are disposed near said model 35. To avoid a kinking and blocking of the hoses 33 and 34, each of said hoses is surrounded by a bendable protective tube 36 or 37, which can be held by one hand. In the present embodiment the tubes 36 and 37 are held together by a clip 38 so that the nozzles 33a and 34a can be moved by hand whereas the rates at which the powder and liquid are discharged are controlled by the foot-operated bellows. The hoses 33 and 34 consist of polytetrafluoroethylene so that they will not be corroded. The operator of the dispenser can simply change the length of the hoses 33 and 34 so that they have the desired length for the sprinkling of powder and for the discharge of the liquid in drops onto the model. If the discharge end of the powder hose has been clogged by polymerization because of careless work, the hose can be rendered operative in a simple manner in that it is shortened just as the hose for liquid.

What is claimed is:

1. A dispenser for a controlled discharge of polymerizable compositions consisting of a powder and a liquid, respectively, in the making of a plate for dental purposes by forming a layer of said powder on a model, applying said liquid to said layer, and polymerizing said powder and liquid on said model,
   the improvement residing in that said dispenser comprises
   a carrying structure,
   first and second containers for holding said powder and liquid, respectively, which containers are mounted on said carrying structure, said first container having a top inlet and a bottom outlet, said second container having a bottom outlet,
   two discharge lines, each of which is flexible at least in part of its length and is connected to said bottom outlet of one of said containers,
   a foot-operable bellows connected to said top outlet of said first container,
   foot-operable means for controlling the discharge of said liquid from said second container through its bottom outlet and said discharge line connected thereto,
   said bottom outlet of said second container being connected to one of said discharge lines by a spring-loaded, normally closed, pneumatically-operable valve,
   said foot-operable means for controlling the discharge of said liquid from said second container being operable to operate said valve in an opening sense, and
   said foot-operable means for controlling the discharge of said liquid from said second container comprising a second foot-operable bellows.

2. The improvement set forth in claim 1, wherein said second container has a top inlet connected to said second foot-operable bellows.

3. The improvement set forth in claim 1, wherein said valve compriss a diaphragm and a valve cone, which is spring-urged to a closing position in contact with said diaphragm and said second bellows is operable to supply compressed air to said diaphragm for moving said valve cone to an open position.

4. The improvement set forth in claim 1, wherein each of said discharge lines is provided with a discharge nozzle, which is remote from the associated bottom outlet.

5. The improvement set forth in claim 1, wherein said discharge nozzles are mechanically interconnected.

6. The improvement set forth in claim 1, wherein said discharge lines have mechanically interconnected ends remote from said bottom outlets.

7. The improvement set forth in claim 1, wherein at least one additional container for holding a liquid color concentrate is carried by said carrying structure and has a top inlet and a bottom outlet,
   a discharge line which is flexible at least in part of its length is connected to said bottom outlet of said additional container, and
   an additional foot-operable bellows is connected to said top inlet of said additional container.

8. The improvement set forth in claim 1, wherein a plurality of additional containers for holding liquid color concentrates in different colors are carried by said carrying structure and have a top inlet and a bottom outlet each, a discharge line which is flexible at least in part of its length is connected to said bottom outlet of each of said additional containers, and an additional foot-operable bellows is detachably connected to at least one of said additional containers.

9. The improvement set forth in claim 1, wherein said first and second containers are suspended from said carrying structure and connected thereto by a plug joint.

10. The improvement set forth in claim 9, wherein each of said containers has the shape of a bottle.

11. The improvement set forth in claim 1, wherein said carrying structure comprises a hood, which overlies and surrounds said first and second containers and is provided with an exhaust port for withdrawing vapors from the interior of said hood, said carrying structure comprises a platform for supporting said model, and each of said discharge lines has an end portion that is remote from the associated bottom outlet and is movable by hand to a position near said platform.

12. The improvement set forth in claim 1, wherein each of said discharge lines comprises a thinwalled flexible end portion that is remote from the associated bottom outlet and surrounded by a bendable protective tube that is adapted to be held and moved by hand.

13. The improvement set forth in claim 12, wherein said protective tubes are mechanically interconnected.

14. The improvement set forth in claim 1, wherein said discharge lines are made of polytetrafluoroethylene.

15. In a process of making a dental plate by a polymerization of polymerizable compositions consisting of a powder and a liquid, wherein a layer of said powder is formed on a model, said liquid is applied to said layer and said powder and liquid are caused to polymerize on said model, the improvement residing in that said powder and liquid are placed into first and second containers, each of which is connected at its bottom to a discharge line that is flexible at least in part of its length, a foot-operable bellows connected to the top of said first container is operated to supply compressed air to said first container above said powder therein in order to force powder out of said first container through said discharge line connected thereto so as to form said layer on said model, and foot-operable means are operated to control the discharge of said liquid from said second container through said discharge line connected thereto so as to apply said liquid to said layer.

16. The improvement set forth in claim 15, wherein a second foot-operable bellows connected to the top of said second container is operated to supply compressed air to said second container above said liquid therein in order to force liquid out of said second container through said discharge line connected thereto so as to apply said liquid to said layer.

17. The improvement set forth in claim 15, wherein said foot-operable means for controlling the discharge of said liquid from said second container through said discharge line are operated to open a normally closed spring-loaded valve interposed between a bottom outlet of said second container and said discharge line connected thereto.

18. The improvement set forth in claim 15, wherein a liquid color concentrate is placed into an additional container, which is connected at its bottom to an additional discharge line that is flexible at least in part of its length, and an additional foot-operable bellows connected to the top of said additional container is operated to supply compressed air to said additional container above said liquid color concentrate therein in order to force liquid color concentrate out of said additional container through said additional discharge line so as to add said liquid color concentrate to said liquid which has been applied to said layer before said powder and liquid are polymerized on said model.

* * * * *